(12) United States Patent
Prieditis et al.

(10) Patent No.: US 11,783,006 B1
(45) Date of Patent: Oct. 10, 2023

(54) COMPUTERIZED METHODS AND SYSTEMS FOR MACHINE-LEARNED MULTI-OUTPUT MULTI-STEP FORECASTING OF TIME-SERIES DATA

(71) Applicant: Cigna Intellectual Property, Inc., Wilmington, DE (US)

(72) Inventors: Armand E. Prieditis, Arcata, CA (US); John E. Paton, Raleigh, NC (US)

(73) Assignee: Cigna Intellectual Property, Inc., Wilmington, DE (US)

(*) Notice: Subject to any disclaimer, the term of this patent is extended or adjusted under 35 U.S.C. 154(b) by 623 days.

(21) Appl. No.: 16/834,354

(22) Filed: Mar. 30, 2020

Related U.S. Application Data (60) Provisional application No. 62/826,721, filed on Mar. 29, 2019.

(51) Int. Cl.
| | |
|---|---|
| *G16H 50/30* | (2018.01) |
| *G01W 1/10* | (2006.01) |
| *G06F 7/24* | (2006.01) |
| *G06F 17/16* | (2006.01) |
| *G06F 17/18* | (2006.01) |

(52) U.S. Cl.
CPC ............... *G06F 17/18* (2013.01); *G01W 1/10* (2013.01); *G06F 7/24* (2013.01); *G06F 17/16* (2013.01); *G16H 50/30* (2018.01)

(58) Field of Classification Search
CPC ... G06F 17/18; G06F 11/3447; G06F 11/2263; G06F 11/3006; G16H 50/30; G01W 1/10; G06F 7/24; G06F 17/16; G01W 1/00; G01W 1/16; G06Q 10/04; G06N 7/005; Y02A 90/10; Y02E 60/00

USPC .. 702/2-3, 179, 181-182, 186, 189; 703/2, 14-703/15, 21; 73/170.16
See application file for complete search history.

(56) References Cited

U.S. PATENT DOCUMENTS

| | | | | |
|---|---|---|---|---|
| 6,059,724 | A * | 5/2000 | Campell et al. | G16H 50/50 128/923 |
| 10,423,923 | B2 | 9/2019 | Harsha et al. | |
| 2016/0343093 | A1* | 11/2016 | Riland et al. | G06Q 50/06 |
| 2017/0132699 | A1 | 5/2017 | Hagell | |
| 2017/0220926 | A1 | 8/2017 | Chhabra et al. | |

(Continued)

FOREIGN PATENT DOCUMENTS

JP 2001511680 A * 8/2001

*Primary Examiner* — Jeffrey P Aiello
(74) *Attorney, Agent, or Firm* — Miller Johnson (57) ABSTRACT

A forecasting system includes a processor and memory. The memory stores a time-series data store and instructions. The instructions include, in response to receiving a forecasting request from a user device for an entity including input data, determining a measure of uncertainty associated with the input data. The input data includes a proposed action and a forecast period. The instructions include obtaining a set of historical data from the time-series data store associated with the proposed action and generating a forecast model using the set of historical data, the input data, and the measure of uncertainty to predict outcomes incrementally during the forecast period. The instructions include determining a predicted outcome using the forecast model for the entity at an end of the forecast period and, in response to the predicted outcome exceeding a threshold, generating a communication indicating the proposed action and transmitting the communication to the user device.

16 Claims, 4 Drawing Sheets

(56) References Cited

U.S. PATENT DOCUMENTS

| | | | |
|---|---|---|---|
| 2018/0349797 A1* | 12/2018 | Garvey et al. | G06F 9/46 |
| 2019/0188742 A1 | 6/2019 | Vasudevan et al. | |
| 2019/0318434 A1 | 10/2019 | Avey et al. | |
| 2020/0175270 A1* | 6/2020 | McKenna et al. | G06T 7/00 |
| 2020/0309994 A1 | 10/2020 | Eckel et al. | |
| 2020/0320343 A1* | 10/2020 | Cohen et al. | G06Q 30/0202 |

* cited by examiner

COMPUTERIZED METHODS AND SYSTEMS FOR MACHINE-LEARNED MULTI-OUTPUT MULTI-STEP FORECASTING OF TIME-SERIES DATA

CROSS-REFERENCE TO RELATED APPLICATIONS

This application claims the benefit of U.S. Provisional Application No. 62/826,721 filed Mar. 29, 2019. The entire disclosure of the application referenced above is incorporated by reference.

FIELD

The present disclosure relates to time-series forecasting and more particularly to multi-output and multi-step time-series forecasting that produces a probability distribution.

BACKGROUND

A time series is a sequence of measurements (generally historical) of one or more variables at equal time intervals. One of the most frequent uses of time-series data is forecasting the future based on knowledge of the past. Forecasting plays an important role in nearly every field of science and engineering, including healthcare, physics, economics, finance, business, meteorology, and telecommunications.

As an example, the collection of healthcare data has exploded and the need for accurate clinical forecasts based on the collected data is enormous. However, the use of linear statistical models—such as autoregressive integrated moving average (ARIMA) models—have failed to provide accurate forecasts. Although non-linear time-series models such as bilinear models, threshold autoregressive models, and autoregressive conditional heteroscedastic models have been developed, these models are difficult to learn from a given data set.

Multi-output time-series forecasting refers to time-series forecasting with one or more outputs. For example, in healthcare, a multi-output may include blood pressure, heart rate, and blood glucose levels. As another example, with respect to weather forecasting, a multi-output may include temperature, humidity, and barometric pressure. What makes multi-output forecasting difficult is that the outputs are often correlated. Predicting each output independently from each other can result in nonrealistic combinations. Although forecasting for the joint probability of outputs captures all dependencies between output variables, it is computationally infeasible to accomplish even for a small number of outputs.

Multi-step time-series forecasting refers to time-series forecasting more than one interval into the future. What makes multi-step time-series forecasting difficult is that errors can compound and magnify into the future across multiple steps. Moreover, such errors can be difficult to quantify over each step forward.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A forecasting system includes at least one processor and a memory coupled to the at least one processor. The memory stores a time-series data store including historical data relating to a particular category and instructions for execution by the at least one processor. The instructions include, in response to receiving a forecasting request from a user device for an entity including input data, determining a measure of uncertainty associated with the input data. The input data includes a proposed action and a forecast period. The instructions include obtaining a set of historical data from the time-series data store associated with the proposed action and generating a forecast model using the set of historical data, the input data, and the measure of uncertainty to predict outcomes incrementally during the forecast period. The instructions include determining a predicted outcome using the forecast model for the entity at an end of the forecast period and, in response to the predicted outcome exceeding a threshold, generating a communication indicating the proposed action and transmitting the communication to the user device.

In other features, the instructions include, in response to the forecasting request from the user device including a set of entities, for each entity of the set of entities, determining the predicted outcome and adding the predicted outcome to an outcome list. In other features, the instructions include rearranging the outcome list based on a value of each predicted outcome and selecting a reduced set of predicted outcomes greater than the threshold. In other features, the instructions include identifying a reduced set of entities corresponding to each predicted outcome included in the reduced set of predicted outcomes and displaying the reduced set of entities to the user device.

In other features, the instructions include determining another predicted outcome for the entity using another proposed action and calculating a value equal to the predicted outcome less the another predicted outcome. In other features, the instructions include, based on the value, displaying on the user device a likelihood of success of the proposed action. The another proposed action is not performing the proposed action. In other features, the proposed action includes a method of communication, a frequency of communication, and a desired outcome. In other features, the forecast model generates a mean vector and a covariance matrix based on a linear function.

In other features, the covariance matrix is sized based on a sum of a number of input features of the forecast model and a number of output features of the forecast model. In other features, the mean vector includes a mean values and each mean value represents data occurring at a time interval. In other features, the mean vector includes a first piece of data and a second piece of data and the first piece of data represents data occurring a time interval after the second piece of data. In other features, the first piece of data corresponds to output of the forecast model and the second piece of data corresponds to input of the forecast model.

In other features, the covariance matrix includes a first matrix associated with output of the forecast model, a second matrix associated with input of the forecast model, and a third matrix associated with an output relationship between outputs of the forecast model and an input relationship between inputs of the forecast model. In other features, the particular category is related to healthcare, weather, or finances. In other features, the time-series data store is updated at a set time interval. In other features, the entity is a patient and the time-series data store includes time-series data for at least one of a blood pressure, a heart rate, and a blood glucose level of the patient.

A forecasting method includes, in response to receiving a forecasting request from a user device for an entity including input data, determining a measure of uncertainty associated with the input data. The input data includes a proposed action and a forecast period. The method includes obtaining a set of historical data from a time-series data store associated with the proposed action. The time-series data store includes historical data relating to a particular category. The method includes generating a forecast model using the set of historical data, the input data, and the measure of uncertainty to predict outcomes incrementally during the forecast period. The method includes determining a predicted outcome using the forecast model for the entity at an end of the forecast period and, in response to the predicted outcome exceeding a threshold, generating a communication indicating the proposed action and transmitting the communication to the user device.

In other features, the method includes, in response to the forecasting request from the user device including a set of entities, for each entity of the set of entities, determining the predicted outcome and adding the predicted outcome to an outcome list. In other features, the method includes rearranging the outcome list based on a value of each predicted outcome and selecting a reduced set of predicted outcomes greater than the threshold. In other features, the method includes identifying a reduced set of entities corresponding to each predicted outcome included in the reduced set of predicted outcomes and displaying the reduced set of entities to the user device.

In other features, the method includes determining another predicted outcome for the entity using another proposed action, calculating a value equal to the predicted outcome less the another predicted outcome, and, based on the value, displaying on the user device a likelihood of success of the proposed action. The another proposed action is not performing the proposed action. In other features, the proposed action includes a method of communication, a frequency of communication, and a desired outcome.

In other features, the forecast model generates a mean vector and a covariance matrix based on a linear function. In other features, the covariance matrix is sized based on a sum of a number of input features of the forecast model and a number of output features of the forecast model. In other features, the mean vector includes mean values and each mean value represents data occurring at a time interval.

In other features, the mean vector includes a first piece of data and a second piece of data, the first piece of data represents data occurring a time interval after the second piece of data, the first piece of data corresponds to output of the forecast model, and the second piece of data corresponds to input of the forecast model.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

DETAILED DESCRIPTION

Introduction

Based on the above difficulties, what is needed is a forecasting method that can automatically learn from historical data and that: is multi-output, takes into account relationships between the outputs, is multi-step, and produces a probability distribution of the outputs. To meet these needs, the forecasting system of the present disclosure implements machine learning to incrementally compute predictions over a forecasting period to determine or compare an outcome or results of performing a proposed action. For example, the comparison may include performing an intervention or contacting a client versus not contacting the client. In various implementations, the purpose of contacting the client may be to communicate reminders for that client, engage in sales activity, etc. The proposed action may include sending emails, calling, texting, or other forms of contacting a client or individual.

The forecasting system is configured to determine predicted outcomes at set time intervals during the forecasting period. For example, a user may want to determine whether an individual will more closely adhere to a schedule or prescription if the user is contacted by email daily (the proposed action). To predict the outcome (a probability or likelihood of adherence), the forecasting system generates a forecasting model for the individual for the proposed action based on historical time-series data stored in a time-series data store. The forecasting model is built based on historical data related to the proposed action and outputs a predicted outcome at the end of the forecast period. The predicted outcome may be a numerical value indicating a likelihood of a desired outcome.

In various implementations, the predicted outcome can be compared to another predicted outcome to determine the likelihood of the desired outcome occurring without the proposed action. The comparison can indicated whether the proposed action results in the desired outcome. Alternatively, the predicted outcome can be compared to a threshold to determine whether the predicted outcome indicates that the proposed action will be helpful in obtaining the desired outcome.

Forecasting is important in many areas such as weather, agriculture, manufacturing, sales, and the military. As an example, in weather forecasting it might be desirable to forecast the temperature, humidity, and barometric pressure two days from now. The present disclosure facilitates not only forecasting multiple items such as temperature, humidity, and barometric pressure, but knowing how those items are related in terms of their uncertainty. Knowing this uncertainty can facilitate making decisions under risk. Knowing this uncertainty can also facilitate propagating the uncertainty forward in time—for example, using tomorrow's forecast to predict the next day's forecast. The uncertainty is carried forward in time using a compact representation so that the uncertainty does not have to be sampled at each step forward in time.

Figure 1:
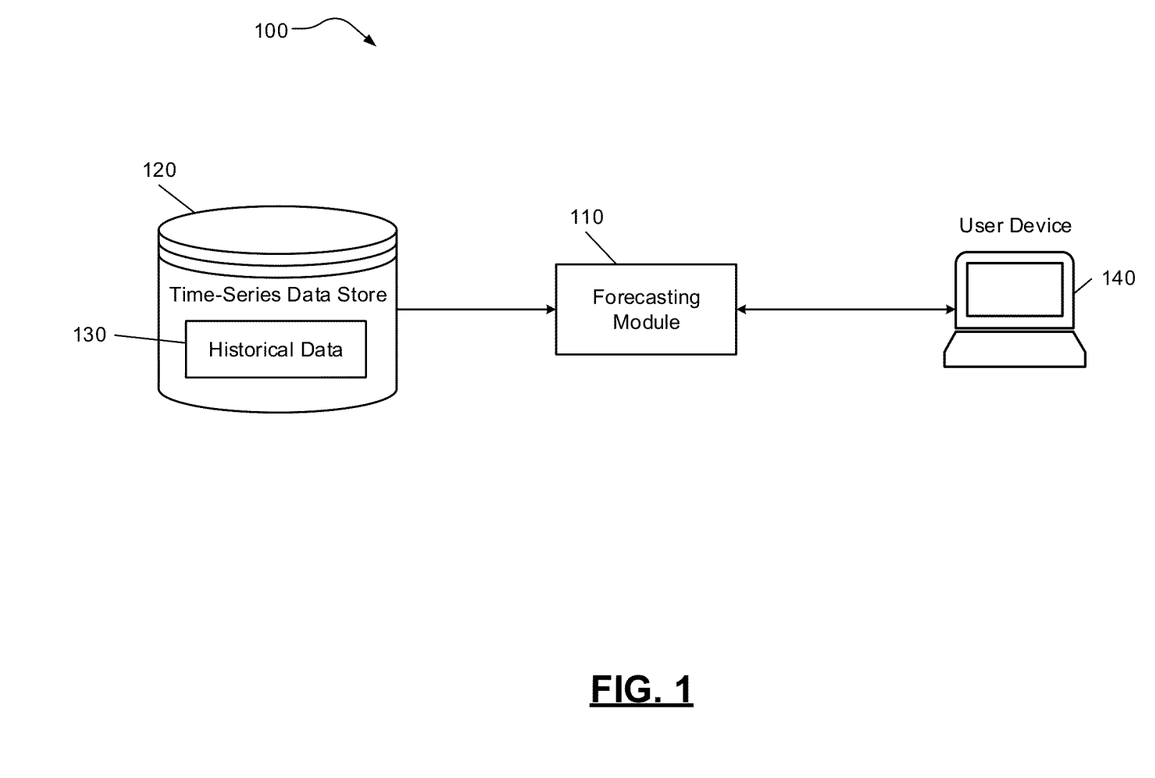
FIG. 1 is a functional block diagram of an example forecasting system according to the principles of the present disclosure.

FIG. 1 is a block diagram of an example forecasting system 100. The forecasting system 100 may include a forecasting module 110 and a time-series data store 120. The time-series data store 120 stores historical data 130. In some implementations, the historical data 130 includes healthcare data. In other implementations, the historical data 130 includes weather data, financial data, and/or another type of data measured at regular time intervals. The historical data 130 may include values for multiple related measurements. For example, healthcare data may include blood pressure, heart rate, and blood glucose level measurements of a patient. As another example, weather data may include average daily temperature, humidity, barometric pressure, etc. The accuracy of a forecast based on the historical data 130 may be directly proportional to the length of time represented by the historical data 130. As an example, five years of weather data typically produces more accurate forecasts than a single month or a single year of weather data.

The forecasting module 110 generates a model of the historical data 130 stored in the time-series data store 120. The model may include an (m+n) × 1 mean vector (μ) and an (m+n) × (m+n) covariance matrix (Σ), where m is the number of input features of the model and n is the number of output features of the model. The model of the historical data 130 stored in the time-series data store 120 may be partitioned as:

$$\mu = \begin{bmatrix} \mu_a \\ \mu_b \end{bmatrix} \quad \Sigma = \begin{bmatrix} \Sigma_a & \Sigma_c \\ \Sigma_c^T & \Sigma_b \end{bmatrix}$$

where $\mu_a$ is an n × 1 mean vector associated with the output of the model and $\mu_b$ is an m × 1 mean vector associated with the input of the model. In other words, $\mu_a$ represents data that occurs one time interval after the data represented by $\mu_b$. In some implementations, $\mu_a$ and $\mu_b$ may include values associated with one time interval or multiple time intervals. As an example only, $\mu_b$ may include 3 years of data, where each year is represented as a separate vector. $\Sigma_a$ is an n × n covariance matrix associated with the output of the model of the historical data 130, $\Sigma_b$ is an m × m covariance matrix associated with the input of the model of the historical data 130, $\Sigma_c$ is an m × m covariance matrix associated with the relationship between the outputs of the model of the historical data 130 (rows) and the inputs of the model of the historical data 130 (columns), and $\Sigma_c^T$ is the transpose of $\Sigma_c$.

The forecasting system 100 may also include a user device 140. The user device 140 may be a desktop computer, a laptop computer, a tablet, a smartphone, or the like. A user may operate the user device 140 to transmit a forecast request to the forecasting module 110. In some implementations, the forecast request may include an m × 1 mean vector input ($\mu_x$) and an m × m covariance matrix ($\Sigma_x$) that represents the uncertainty associated with the values in the mean vector input ($\mu_x$). In other implementations, the forecast request may include input data and a measure of uncertainty associated with the input data. The forecasting module 110 generates the mean vector input ($\mu_x$) and the covariance matrix ($\Sigma_x$) based on the input data and measure of uncertainty included in the forecast request. When the values in the mean vector input ($\mu_x$) are known with complete certainty, $\Sigma_x$ is 0. The forecast request also includes a number of steps (h) that represents the number of time intervals in the future of the requested prediction. In some implementations, the forecast request includes the model of the historical data 130 stored in the time-series data store 120.

In response to receiving the forecast request, the forecasting module 110 generates a prediction based on the historical data 130 stored in the time-series data store 120. The prediction generated by the forecasting module 110 includes a mean vector and an associated covariance matrix. The forecasting module 110 may use a linear function (f) to generate the mean vector and the covariance matrix of the prediction. The function f may be defined by Equations 1-5.

$$f(\mu_x, \Sigma_x, h) = (\mu_{x,h}, \Sigma_{x,h}) \quad (1)$$

$$\mu_{x,h} = (M)^h \mu_x + (I-M)^{-1}(I-M)^h (\mu_b - M^h \mu_b) \quad (2)$$

$$\Sigma_{x,h} = M^h \Sigma_x M^{h^T} + \\ unvec\left[(M \otimes M - I)^{-1} vec(M^{h+1} C M^{h+1^T}) - C\right] \quad (3)$$

$$M = \Sigma_c \Sigma_b^{-1} \quad (4)$$

$$C = \Sigma_a - \Sigma_c \Sigma_b^{-1} \Sigma_c^T \quad (5)$$

$\mu_{x,h}$ is the predicted mean vector h steps (time intervals) in the future and $\Sigma_{x,h}$ is the associated covariance matrix. $\mu_a$, $\mu_b$, $\Sigma_a$, $\Sigma_b$, $\Sigma_c$, and $\Sigma_c^T$ refer to the model of the historical data 130. The forecasting module 110 may use the historical data 130 to determine the values of $\mu_a$, $\mu_b$, $\Sigma_a$, $\Sigma_b$, $\Sigma_c$, and $\Sigma_c^T$. The forecasting module 110 may store the determined values for later use. In response to determining that the historical data 130 has changed—for example, the new data is stored in the time-series data store 120—the forecasting module 110 may determine and store new values for $\mu_a$, $\mu_b$, $\Sigma_a$, $\Sigma_b$, $\Sigma_c$, and $\Sigma_c^T$. I is the identity matrix, vec() is a function that unstacks a matrix into a column vector, and univec() is a function that stacks a column vector into a matrix. Stated another way, unvec() is the inverse function of vec(). The symbol ⊗ signifies the Kronecker product of two matrices, T signifies the transpose of a matrix, and -1 signifies matrix inversion. If the inputs to the function f are empty, the function f returns $\mu_a$ and $\Sigma_a$ as the mean vector and associated covariance matrix, respectively.

The forecasting module 110 uses the function f and the model of the historical data 130 to generate a mean vector and an associated covariance matrix that incorporate the distributions captured by the model. For example, the forecasting module 110 may use Equation 6 to generate the prediction.

$$f(\mu_x, \Sigma_x, h) = \begin{cases} (\mu_x, \Sigma_x) & \text{if } h = 0 \\ f\left(\underbrace{\mu_a}_{1} + \underbrace{\Sigma_c \Sigma_b^{-1}(\mu_x - \mu_b)}_{2}, \underbrace{\Sigma_a}_{3} - \underbrace{\Sigma_c \Sigma_b^{-1} \Sigma_c^T}_{4} \\ + \underbrace{(\Sigma_c \Sigma_b^{-1}) \Sigma_x (\Sigma_c \Sigma_b^{-1})^T}_{5}, h-1 \right) & \text{otherwise} \end{cases} \quad (6)$$

When h is zero, the forecasting module 110 will provide the mean vector input ($\mu_x$) and an m × m covariance matrix ($\Sigma_x$) included in the forecast request as the predicted mean vector and associated covariance matrix. When h is equal to any value other than zero, the forecasting module 110 uses the specified inputs for the function f to generate the prediction.

In Equation 6, $\mu_a$ (labeled as 1) is the mean vector associated with the output of the model of the historical data 130. Item 1 represents the average output of the model. $\mu_a$ is adjusted by the effect of the input (labeled as 2) and is used as the first input for the function f. Item 2 represents an adjustment to the average output based on the covariance between a given input and the output of the model. $\Sigma_a$ (labeled as 3) is the distribution (covariance) associated with the output of the model of the historical data 130. $\Sigma_a$ is adjusted by the posterior distribution (labeled as 4) and a term (labeled as 5) that takes into account the distribution of the inputs ($\Sigma_x$). Subtracting the posterior distribution sharpens $\Sigma_a$ — in other words, it makes $\Sigma_a$ less diffused. Item 4 represents an adjustment of the covariance associated with the average output based on the uncertainty of the inputs and outputs of the model. Item 5 represents an adjustment to the covariance associated with the average output based on the uncertainty associated with the given input. The adjusted $\Sigma_a$ is used as the second input for the function f and h-1 is used as the third input for the function f.

The forecasting module 110 may use a non-linear function to generate the prediction. In some implementations, the forecasting module 110 may use a non-linear form of the function f by applying multiple Gaussian mixture distributions to the function f. For example, the forecasting module 110 may use Equation 7 to generate the prediction.

$$f(\mu_x, \Sigma_x, h) = \begin{cases} (\mu_x, \Sigma_x) & \text{if } h=0 \\ f\left(\begin{array}{c} \sum_{i=1}^{k} p_i(\mu_x)\left(\mu_{a_i} + \Sigma_{c_i}\Sigma_{b_i}^{-1}(\mu_x - \mu_{b_i})\right), \\ \sum_{i=1}^{k} p_i(\mu_x)\left(\begin{array}{c}\Sigma_{a_i} - \Sigma_{c_i}\Sigma_{b_i}^{-1}\Sigma_{c_i}^{T} + \\ \left(\Sigma_{c_i}\Sigma_{b_i}^{-1}\right)\Sigma_x\left(\Sigma_{c_i}\Sigma_{b_i}^{-1}\right)^{T}\end{array}\right), h-1 \end{array}\right) & \text{otherwise} \end{cases} \quad (7)$$

k represents the number of Gaussian mixture distributions applied to the function f. The forecasting module 110 may derive each applied Gaussian mixture distribution from the historical data 130. In some implementations, the forecasting module 110 may use the Expectation-Maximization algorithm to determine the Gaussian mixture distributions. In some implementations, the forecasting module 110 may use other techniques and/or algorithms—such as k-means—to determine the Gaussian mixture distributions. $p_i(\mu_x)$ returns the probability of the $i^{th}$ Gaussian mixture distribution with respect to the input included in the forecast request ($\mu_x$). Each Gaussian mixture distribution includes its own mean vectors ($\mu$) and associated covariance matrices ($\Sigma$), which are indexed by the mixture number (i).

In some implementations, the forecasting module 110 may apply a single Gaussian mixture distribution to the function f. Specifically, the forecasting module 110 uses the mean vector ($\mu$) and associated covariance matrices ($\Sigma$) of the most likely Gaussian mixture distribution—in other words, the Gaussian mixture distribution that returns the highest probability for the input included in the forecast request ($\mu_x$). For example, the forecasting module 110 may use Equation 8 to generate the prediction.

$$f(\mu_x, \Sigma_x, h) = \begin{cases} (\mu_x, \Sigma_x) & \text{if } h=0 \\ f\left(\begin{array}{c} \mu_{a_{l(\mu_x)}} + \Sigma_{c_{l(\mu_x)}}\Sigma_{b_{l(\mu_x)}}^{-1}\left(\mu_x - \mu_{b_{l(\mu_x)}}\right), \\ \Sigma_{a_{l(\mu_x)}} - \Sigma_{c_{l(\mu_x)}}\Sigma_{b_{l(\mu_x)}}^{-1}\Sigma_{c_{l(\mu_x)}}^{T} + \\ \left(-\Sigma_{c_{l(\mu_x)}}\Sigma_{b_{l(\mu_x)}}^{-1}\right)\Sigma_x\left(-\Sigma_{c_{l(\mu_x)}}\Sigma_{b_{l(\mu_x)}}^{-1}\right)^{T}, h-1 \end{array}\right) & \text{otherwise} \end{cases} \quad (8)$$

$l(\mu_x)$ returns the mixture number of the most likely Gaussian mixture distribution for the input included in the forecast request ($\mu_x$).

In various implementations, the input included in the forecast request ($\mu_x$) may be a vector of vectors, where each top-level vector in $\mu_x$ includes input values that correspond to a single time interval. For example, the first vector in $\mu_x$ may include values that correspond to the oldest data in the input, the second vector in $\mu_x$ may include values that correspond to the second oldest data in the input, ... and the last vector in $\mu_x$ may include values that correspond to the most recent data in the input. The forecasting module 110 may use Equation 9 to generate the prediction.

$$f(\mu_x, \Sigma_x, h) = \begin{cases} (\mu_x, \Sigma_x) & \text{if } h=0 \\ f\left(\begin{array}{c} \left[\begin{array}{c}\mu_a + \Sigma_c\Sigma_b^{-1}(\mu_x - \mu_b)\\ \mu_x[1:]\end{array}\right], \\ \Sigma_{a\|x} - \Sigma_{c\|x}\Sigma_b^{-1}\Sigma_{c\|x}^{T} + \left(\Sigma_{c\|x}\Sigma_b^{-1}\right)\Sigma_x\left(\Sigma_{c\|x}\Sigma_b^{-1}\right)^{T}, h-1 \end{array}\right) & \text{otherwise} \end{cases} \quad (9)$$

$\mu_x[1:]$ represents all of the values in the input included in the forecast request ($\mu_x$) other than the values that correspond to the oldest time-series interval. In other words, $\mu_x[1:]$ represents all but the first vector included in $\mu_x$. $\Sigma_{a\|x}$ and $\Sigma_{c\|x}$ may be expressed as Equations 10 and 11, respectively.

$$\Sigma_{a\|x} = \begin{bmatrix} \Sigma_a & \Sigma_{a,x[1:]} \\ \Sigma_{a,x[1:]}^{T} & \Sigma_{x[1:]} \end{bmatrix} \quad (10)$$

$$\Sigma_{c\|x} = \begin{bmatrix} \Sigma_c \\ \Sigma_{c,x[1:]} \end{bmatrix} \quad (11)$$

$\Sigma_{a\|x[1:]}$ is a covariance matrix in which the rows correspond to the output of the model of the historical data 130 and in which the columns correspond to all but the first vector in $\mu_x$. $\Sigma_{x[1:]}$ is a covariance matrix in which both the rows and columns correspond to all but the first vector in $\mu_x$. $\Sigma_{c\|x[1:]}$ is a covariance matrix in which the rows correspond to all but the first vector in $\mu_x$ and the columns correspond to all of the vectors in $\mu_x$.

In some implementations, the forecasting module 110 may apply a plurality of Gaussian mixture distributions (as described in Equation 7) to the inputs of the function f in Equation 9 to generate the prediction. In other implementations, the forecasting module 110 may apply a single Gaussian mixture distribution (as described in Equation 8) to the inputs of the function f in Equation 9 to generate the prediction.

The forecasting module 110 may transmit the generated prediction to the user device 140 in response to receiving the forecast request. The user may use the user device 140 to make a risk-inclusive decision based on the received mean vector and the associated covariance matrix. The user device 140 may determine the maximum expected values of the prediction based on the mean vector (μ) and associated covariance matrix (Σ) received from the forecasting module 110. For example, the user device 140 may use Equation 12 to determine the maximum expected values.

$$min ExpectedValues = (\mu + V\Sigma)W \quad (12)$$

V is a first weighting factor vector of the covariance matrix (Σ)—for example, the level of risk associated with each element in the covariance matrix (Σ) that the decision maker is willing to take. W is a second weighting factor vector that defines how the target variables are to be combined —in other words, how to combine the values in the mean vector (μ).

The user device 140 may also determine the minimum expected values of the prediction based on the mean vector (μ) and associated covariance matrix (Σ) received from the forecasting module 110. For example, the user device 140 may use Equation 13 to determine the minimum expected values.

$$max ExpectedValues = (\mu - V\Sigma)W \quad (13)$$

In some implementations, the forecast request may include the first weighting factor vector, the second weighting factor vector, and an indication whether the predicted values should be maximized or minimized. In response to the forecast request indicating that the predicted values should be minimized, the forecasting module 110 may use Equation 12 to determine the minimum expected values of the generated prediction. The forecasting module 110 may transmit the determined minimum expected values to the user device 140 in response to receiving the forecast request. In response to the forecast request indicating that the predicted values should be maximized, the forecasting module 110 may use Equation 13 to determine the maximum expected values of the generated prediction. The forecasting module 110 may transmit the determined maximum expected values to the user device 140 in response to receiving the forecast request.

In some implementations, the forecast request may include a confidence percentage and the forecasting module 110 may determine a confidence interval based on the generated prediction and the received confidence percentage. In other implementations, the user device 140 may determine a confidence interval based on the prediction received from the forecasting module 110 and a percentage provided by the user.

In various implementations, a web portal (not shown) may be implemented to allow the user of the user device 140 to submit requests using a web interface. The web portal may be collocated with the forecasting module 110 or implemented separately. The web portal may graphically plot forecasted data in a web interface presented to the user of the user device 140. The plot may represent confidence intervals graphically such as by using error bars. The web portal may, additionally or alternatively, allow for download of the prediction data, such as in JSON (JavaScript Object Notation) format or CSV (comma-separated values) format. The web portal may also allow the user to formulate an API (application programming interface) request to programmatically supply requests and receive forecast data. API calls may be serviced by the web portal or by a separate application server.

Flowcharts

Figure 2:
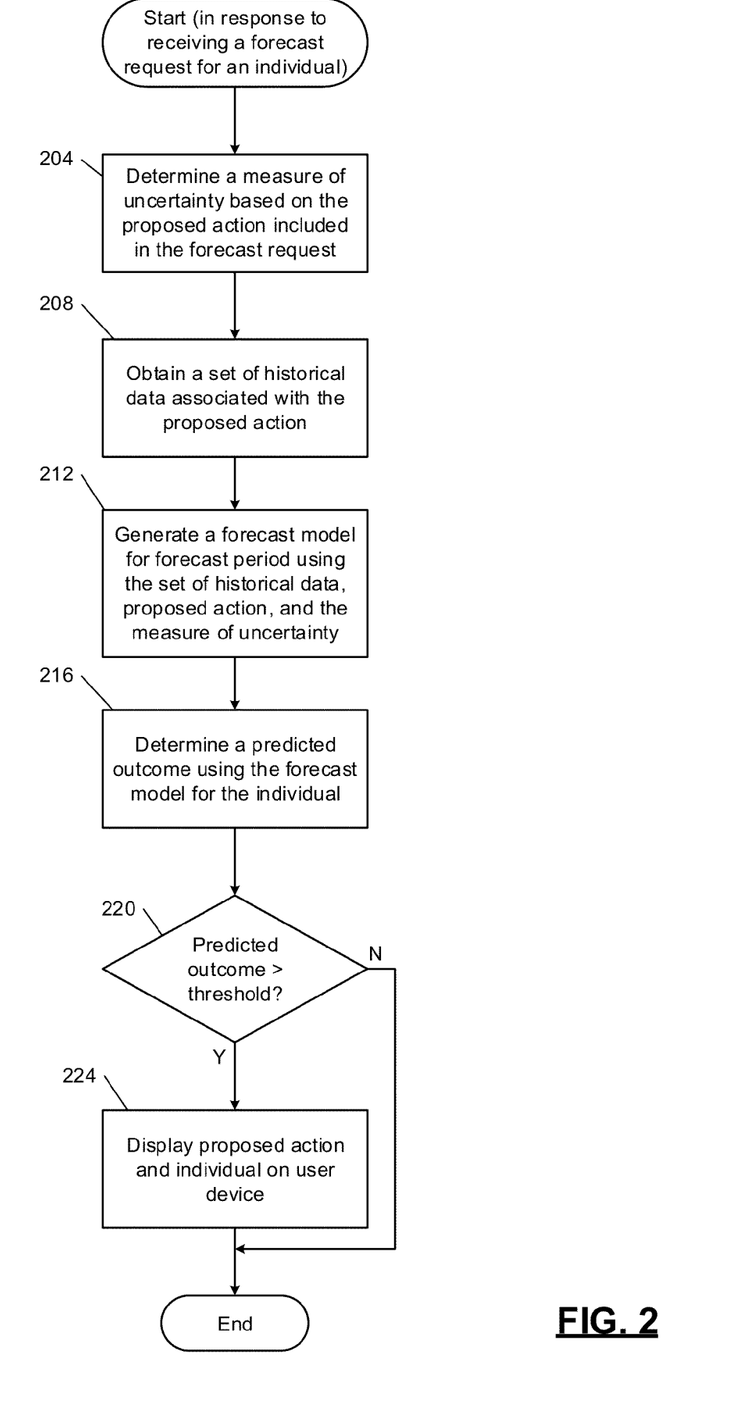
FIG. 2 is a flowchart of example outcome prediction for an individual according to the principles of the present disclosure.

FIG. 2 is a flowchart of example outcome prediction for an individual according to the principles of the present disclosure. Control begins in response to receiving a forecast request for an individual. The forecast request may include input data, such as a proposed action, including a forecast period, a time interval, and a desired outcome. At 204, control determines a measure of uncertainty based on the proposed action included in the forecast request. A user is submitting the forecast request via a user device to determine whether a proposed action will result in the desired outcome.

Then, control continues to 208 to obtain a set of historical data associated with the proposed action. As described previously, the proposed action includes many variables; for example, a user may want to determine whether an individual will more closely adhere to a schedule or prescription (desired outcome) if the user is contacted by email (method) daily (time interval), together a proposed action. Therefore, historical data relating to the proposed action is identified and implemented by control to determine the predicted outcome.

At 212, control generates a forecast model for the forecast period using the set of historical data, proposed action, and the measure of uncertainty. That is, the forecast model is generated to determine the likelihood of a desired outcome or the predicted outcome of the proposed action for the individual occurring or having the intended result at an end of the forecast period. Control continues to 216 to determine predicted outcome using the forecast model for the individual. In various implementations, the predicted outcome is a value indicating the likelihood that the desired outcome will occur if the method and time interval are implemented. That is, the predicted outcome is a measure of how effective the proposed action will be.

Control proceeds to 220 to determine whether the predicted outcome is greater than a threshold. The threshold indicates a barrier at which, when below, the likelihood of the proposed action resulting in the desired outcome is no longer viable based on, for example, an amount of resources used to perform the proposed action. Therefore, if the predicted outcome is less than the threshold, control ends. Otherwise, if the predicted outcome is greater than the threshold, then control continues to 224 to display the proposed action and the individual on a user device. In various implementations, the user device submits the forecast request. Then, control ends.

Figure 3:
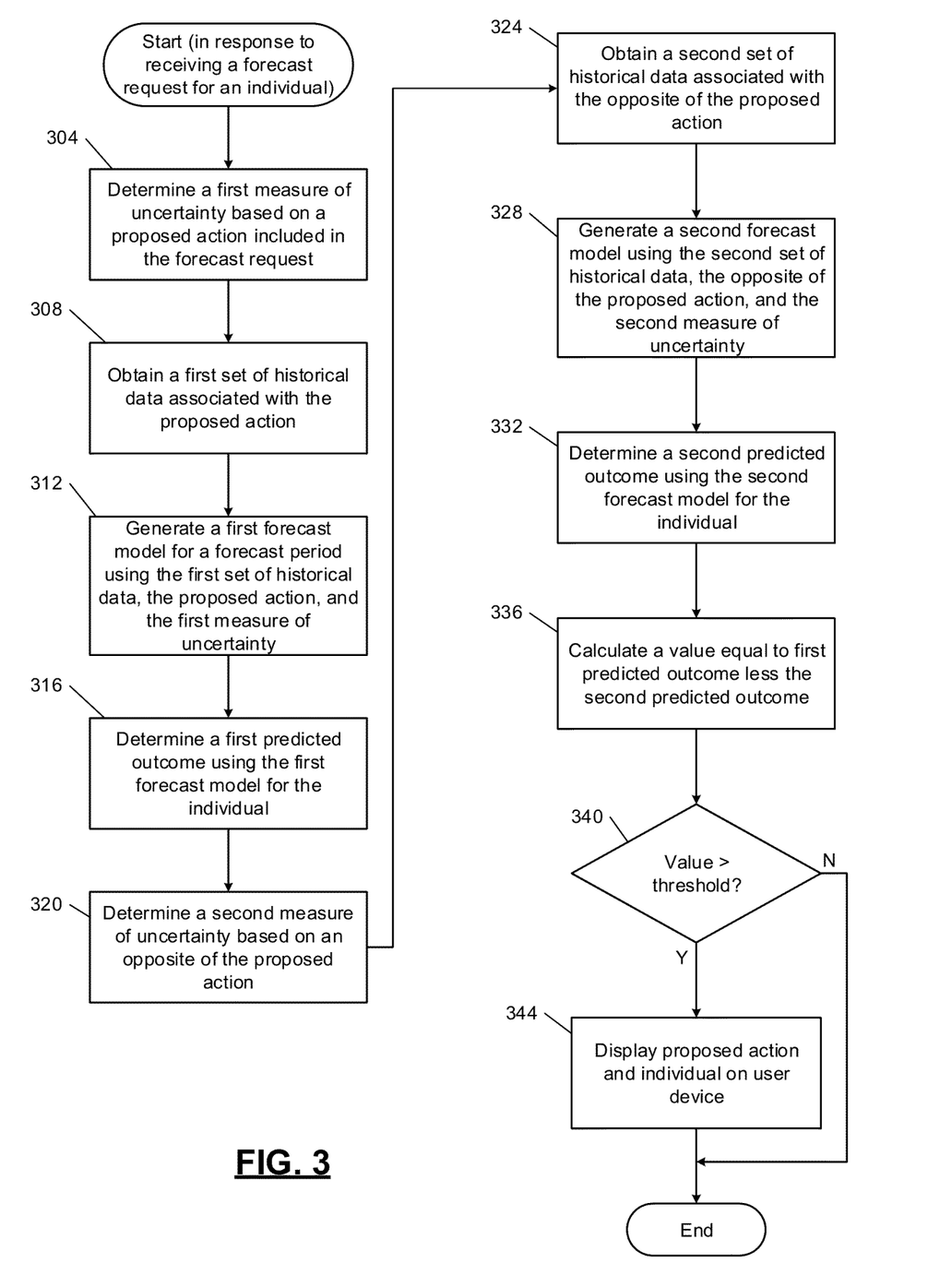
FIG. 3 is a flowchart of example outcome prediction comparison for an individual according to the principles of the present disclosure.

FIG. 3 is a flowchart of example outcome prediction comparison for an individual according to the principles of the present disclosure. Control begins in response to receiving a forecast request for an individual. As described above, the forecast request may include input data, such as a proposed action. Control continues to 304 to determine a first measure of uncertainty based on a proposed action included in the forecast request. Control continues to 308 to obtain a first set of historical data associated with the proposed action.

Then, control continues to 312 to generate a first forecast model for a forecast period using the first set of historical data, the proposed action, and the first measure of uncertainty. Control proceeds to 316 to determine a first predicted outcome using the first forecast model for the individual. At 320, control determines a second measure of uncertainty based on an opposite of the proposed action. In various implementations, the opposite of the proposed action is the absence of the performance of the proposed action, for example, not calling daily but having the same desired outcome. For example, the opposite of the proposed action may be simply a lack of action but still having the same desired outcome.

Control proceeds to 328 to generate a second forecast model using the second set of historical data, the opposite of the proposed action, and the second measure of uncertainty. As mentioned previously, both the proposed action and the opposite of the proposed action are going to have the same desired outcome. Control proceeds to 332 to determine a second predicted outcome using the second forecast model for the individual. Then, at 336, control calculates a value equal to the first predicted outcome less the second predicted outcome. This compares the difference between performing some type of action of method to prompt the desired outcome and doing nothing with the hope that the desired outcome will occur.

Then, control continues to 340 to determine whether the value is greater than a threshold. Since the two models are determining predicted outcomes or a likelihood of the action results in the desired outcome occurring, a greater value suggests that performing the proposed action is more likely to result in the desired outcome while a lower value suggests that doing nothing will result in the desired outcome. If no, control ends. Otherwise, if yes, control continues to 344 to display the proposed action and individual on the user device transmitting the forecast request. Then, control ends. In various implementations, control may also set up reoccurring reminders or automated emails at 344.

Figure 4:
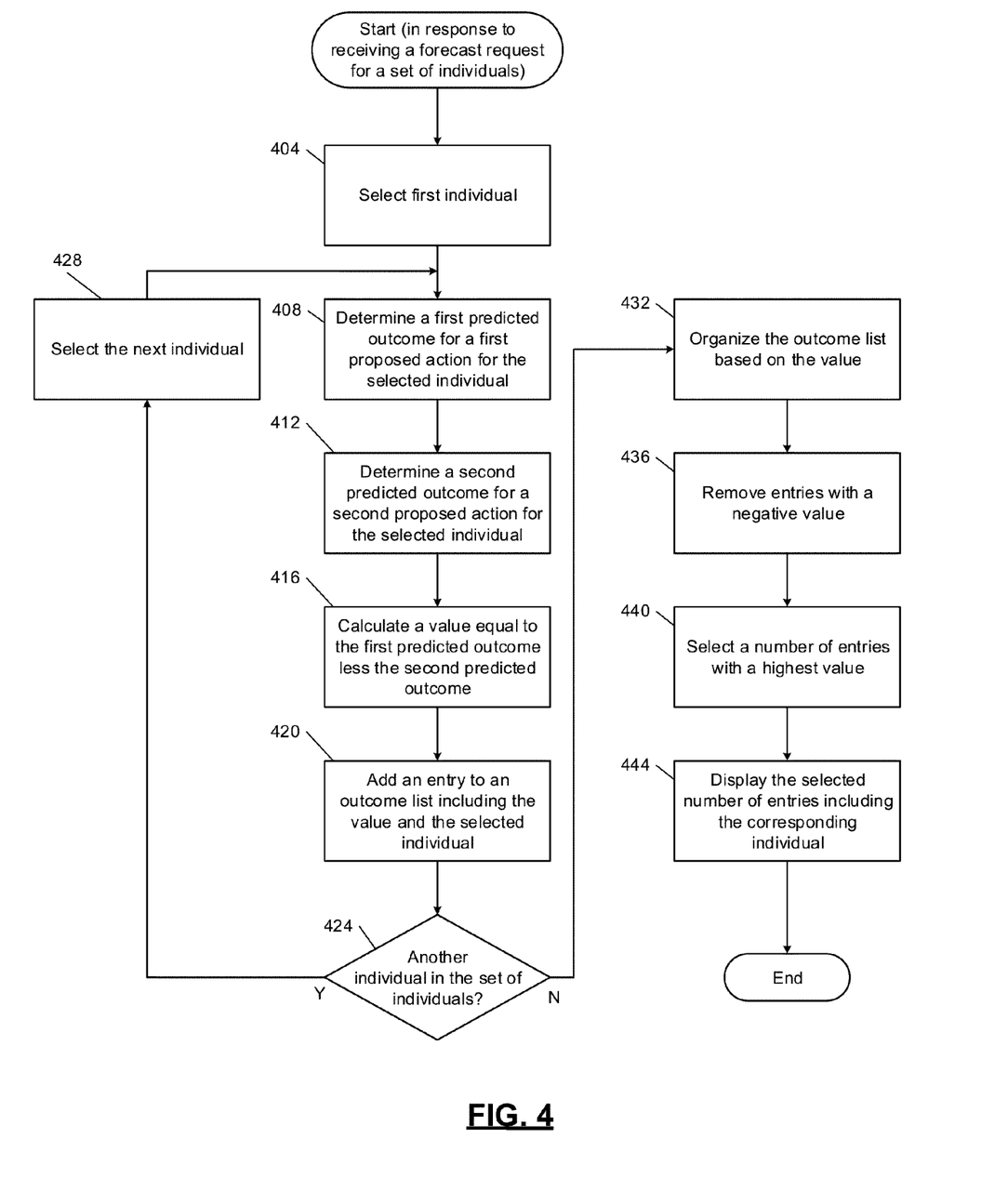
FIG. 4 is a flowchart of example outcome prediction list generation for a set of individuals according to the principles of the present disclosure.

FIG. 4 is a flowchart of example outcome prediction list generation for a set of individuals according to the principles of the present disclosure. Control begins in response to receiving a forecast request for a set of individuals. At 404, control selects the first individual. Then, control determines a first predicted outcome for a first proposed action for the selected individual at 408.

Then, at 412, control determines a second predicted outcome for a second proposed action for the selected individual. As described in FIGS. 2 and 3, determining predicting outcomes involves generating forecast models based on historical data. Then, at 416, control calculates a value equal to the first predicted outcome less the second predicted outcome. In various implementations, control determines a difference between the first predicted outcome and the second predicted outcome to identify which proposed action (the first or the second) is the better procedure.

Control proceeds to 420 to add an entry to an outcome list including the value and the selected individual. Then, control continues to 424 to determine if another individual is in the set of individuals. If yes, control continues to 428 to select the next individual of the set of individuals and return to 408. Otherwise, control proceeds to 432 to organize or sort the outcome list based on the value. Then, at 436, control removes entries with a negative value. At 440, control selects a number of entries with a highest value. Then, at 444, control displays the selected number of entries including the individual corresponding to each entry. Then, control ends.

Conclusion

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

Some or all hardware features of a module may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a module may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A forecasting system comprising:
   at least one processor and
   memory coupled to the at least one processor,
   wherein the memory stores:
      a time-series data store including historical data relating to a particular category and
      instructions for execution by the at least one processor and
   wherein the instructions include, in response to receiving a forecasting request at a web portal, wherein the forecasting request is submitted from a user device for an entity, and wherein the forecasting request includes (i) an input vector and (ii) a number of steps representing a number of future time intervals of the forecasting request:
      determining a measure of uncertainty associated with the input data, wherein the measure of uncertainty includes a compact representation of uncertainty associated with each of the number of future time intervals of the forecasting request;
      obtaining a set of historical data from the time-series data store associated with a proposed action;
      generating a forecast model using the set of historical data, the input data, and the measure of uncertainty to predict outcomes incrementally for the future time intervals of the forecasting request, wherein:
the forecast model generates a mean vector and a predicted uncertainty measure based on a linear function,
the predicted uncertainty measure is generated based on the compact representation of uncertainty,
the mean vector includes a plurality of mean values,
each mean value of the plurality of mean values represents data occurring at a time interval, and
the compact representation of uncertainty is carried forward for each of the number of future time intervals of the forecasting request;
determining a predicted outcome using the forecast model for the entity at an end of the future time intervals of the forecasting request, wherein the predicted outcome is multi-output and multi-step; and
in response to the predicted outcome exceeding a threshold:
generating a communication indicating the proposed action,
transmitting the communication to the user device, and
presenting, via the web portal, a web interface at the user device including (i) a graphical representation of the mean vector generated by the forecast model and (ii) error bars representing values of the predicted uncertainty measure.

2. The system of claim 1 wherein the instructions include, in response to the forecasting request from the user device including a set of entities:
for each entity of the set of entities:
determining the predicted outcome and
adding the predicted outcome to an outcome list;
rearranging the outcome list based on a value of each predicted outcome;
selecting a reduced set of predicted outcomes greater than the threshold;
identifying a reduced set of entities corresponding to each predicted outcome included in the reduced set of predicted outcomes; and
displaying the reduced set of entities to the user device.

3. The system of claim 1 wherein the instructions include:
determining a second predicted outcome for the entity using a second proposed action;
calculating a value equal to the predicted outcome less the second predicted outcome; and
based on the value, displaying on the user device a likelihood of success of the proposed action, wherein performing the second proposed action excludes performing the proposed action.

4. The system of claim 1 wherein the proposed action includes at least one of a method of communication, a frequency of communication, and a desired outcome.

5. The system of claim 1 wherein the predicted uncertainty measure is sized based on a sum of a number of input features of the forecast model and a number of output features of the forecast model.

6. The system of claim 1 wherein:
the mean vector includes a first piece of data and a second piece of data,
the first piece of data represents data occurring a time interval after the second piece of data,
the first piece of data corresponds to output of the forecast model, and the second piece of data corresponds to input of the forecast model.

7. The system of claim 1 wherein the predicted uncertainty measure includes:
a first matrix associated with output of the forecast model,
a second matrix associated with input of the forecast model, and
a third matrix associated with an output relationship between outputs of the forecast model and an input relationship between inputs of the forecast model.

8. The system of claim 1 wherein the particular category is related to at least one of healthcare and weather.

9. The system of claim 1 wherein the time-series data store is updated at a set time interval.

10. The system of claim 1 wherein:
the entity is a patient and
the time-series data store includes time-series data for at least one of a blood pressure, a heart rate, and a blood glucose level of the patient.

11. A forecasting method comprising:
in response to receiving a forecasting request at a web portal, wherein the forecasting request is submitted from a user device for an entity including input data, and wherein the forecasting request includes (i) an input vector and (ii) a number of steps representing a number of future time intervals of the forecasting request:
determining a measure of uncertainty associated with the input data, wherein the measure of uncertainty includes a compact representation of uncertainty associated with each of the number of future time intervals of the forecasting request;
obtaining a set of historical data from a time-series data store associated with a proposed action, wherein the time-series data store includes historical data relating to a particular category;
generating a forecast model using the set of historical data, the input data, and the measure of uncertainty to predict outcomes incrementally for the future time intervals of the forecasting request, wherein:
the forecast model generates a mean vector and a predicted uncertainty measure based on a linear function,
the predicted uncertainty measure is generated based on the compact representation of uncertainty,
the mean vector includes a plurality of mean values,
each mean value of the plurality of mean values represents data occurring at a time interval, and
the compact representation of uncertainty is carried forward for each of the number of future time intervals of the forecasting request;
determining a predicted outcome using the forecast model for the entity at an end of the future time intervals of the forecasting request, wherein the predicted outcome is multi-output and multi-step; and
in response to the predicted outcome exceeding a threshold:
generating a communication indicating the proposed action, transmitting the communication to the user device, and
presenting, via the web portal, a web interface at the user device including (i) a graphical representation of the mean vector generated by the forecast model and (ii) error bars representing values of the predicted uncertainty measure.

12. The method of claim 11 further comprising, in response to the forecasting request from the user device including a set of entities:
for each entity of the set of entities:
determining the predicted outcome and
adding the predicted outcome to an outcome list;
rearranging the outcome list based on a value of each predicted outcome;

selecting a reduced set of predicted outcomes greater than the threshold;

identifying a reduced set of entities corresponding to each predicted outcome included in the reduced set of predicted outcomes; and displaying the reduced set of entities to the user device.

13. The method of claim 11 further comprising:

determining a second predicted outcome for the entity using a second proposed action;

calculating a value equal to the predicted outcome less the second predicted outcome; and based on the value, displaying on the user device a likelihood of success of the proposed action, wherein the second proposed action excludes the proposed action.

14. The method of claim 11 wherein the proposed action includes a method of communication, a frequency of communication, and a desired outcome.

15. The method of claim 11 wherein the predicted uncertainty measure is sized based on a sum of a number of input features of the forecast model and a number of output features of the forecast model.

16. The method of claim 11 wherein: the mean vector includes a first piece of data and a second piece of data, the first piece of data represents data occurring a time interval after the second piece of data, the first piece of data corresponds to output of the forecast model, and the second piece of data corresponds to input of the forecast model.

* * * * *